United States Patent [19]

Tierney et al.

[11] Patent Number: 5,384,335
[45] Date of Patent: Jan. 24, 1995

[54] METHANOL SYNTHESIS USING A CATALYST COMBINATION OF ALKALI OR ALKALINE EARTH SALTS AND REDUCED COPPER CHROMITE

[75] Inventors: John W. Tierney; Irving Wender; Vishwesh M. Palekar, all of Pittsburgh, Pa.

[73] Assignee: University of Pittsburgh, Pittsburgh, Pa.

[21] Appl. No.: 40,644

[22] Filed: Mar. 31, 1993

Related U.S. Application Data

[62] Division of Ser. No. 675,139, Mar. 26, 1991, Pat. No. 5,221,652.

[51] Int. Cl.[6] .................. C07C 29/08; C07C 29/154; C07C 29/16
[52] U.S. Cl. .................................... 518/700; 568/885
[58] Field of Search ...................... 518/700; 568/885

[56] References Cited

U.S. PATENT DOCUMENTS

| | | |
|---|---|---|
| 3,179,706 | 4/1965 | Lee . |
| 3,374,184 | 3/1963 | McEvoy et al. . |
| 4,031,123 | 6/1977 | Espino et al. ........................ 518/700 |
| 4,567,204 | 1/1986 | Mednick et al. .................... 518/700 |
| 4,731,386 | 3/1988 | Onsager . |
| 5,030,609 | 7/1991 | Turner et al. . |
| 5,079,267 | 1/1992 | Kao et al. . |

FOREIGN PATENT DOCUMENTS 1175798 10/1984 Canada .

OTHER PUBLICATIONS

Santos, "Coal Gasification & Methanol Production" Symposium on Energy Production Processes for the Institution of Chemical Engineers in London England Apr. 12–14, 1988.
Monts et al., Applied Catalysis, 22, 1986 pp. 123–136.
Wainwright, Catalytic Processes for Methanol Synthesis, Elsevier Science Publishers Amsterdam 1988 pp. 95–108.

*Primary Examiner*—Howard T. Mars
*Attorney, Agent, or Firm*—Reed Smith Shaw & McClay

[57] ABSTRACT

The present invention relates to a novel route for the synthesis of methanol, and more specifically to the production of methanol by contacting synthesis gas under relatively mild conditions in a slurry phase with a catalyst combination comprising reduced copper chromite and basic alkali salts or alkaline earth salts. The present invention allows the synthesis of methanol to occur in the temperature range of approximately 100°–160° C. and the pressure range of 40–65 atm. The process produces methanol with up to 90% syngas conversion per pass and up to 95% methanol selectivity. The only major by-product is a small amount of easily separated methyl formate. Very small amounts of water, carbon dioxide and dimethyl ether are also produced. The present catalyst combination also is capable of tolerating fluctuations in the $H_2/CO$ ratio without major deleterious effect on the reaction rate. Furthermore, carbon dioxide and water are also tolerated without substantial catalyst deactivation.

20 Claims, No Drawings

METHANOL SYNTHESIS USING A CATALYST COMBINATION OF ALKALI OR ALKALINE EARTH SALTS AND REDUCED COPPER CHROMITE

The subject invention was made in part with Government support under Subcontract No. DE-FG22-89PC89786 awarded by the Department of Energy. The Government has certain rights in this invention.

This is a divisional of copending application(s) Ser. No. 07/675,139 filed on Mar. 26, 1991, now U.S. Pat. No. 5,221,652.

FIELD OF THE INVENTION

The present invention relates to a novel route for synthesizing methanol. Specifically the invention relates to the production of methanol using a combination of a copper chromite catalyst and a basic alkali or alkaline earth compound.

BACKGROUND OF THE INVENTION

Hydrocarbon mixtures such as gasoline and more recently diesel and jet fuels have served as transportation fuels for many years. Recent social and environmental concerns, particularly with respect to $NO_x$ and hydrocarbon gas emissions, however, have led to growing demand for alternate, cleaner burning fuels. Similarly, erosion of the ozone layer in the atmosphere and acid rain have led to a strong demand for controlled atmospheric emissions.

In this context, fuel oxygenates, particularly alcohols have emerged as strong contenders in the quest to develop cleaner burning fuels. Methanol is the cheapest and the most abundant of these alcohols. Favorable factors of methanol include its high octane rating, its manufacture from abundant natural resources (e.g. coal, gas, petroleum fractions, residual biomass and other agricultural products) and its ability to lessen environmental damage.

The current U.S. consumption of methanol is 1.3 billion gallons/yr., while the current U.S. gasoline consumption is 122 billion gallons/yr. Thus, it is likely that methanol will become a very important motor fuel or motor fuel supplement in the future.

Moreover, methanol can undergo a variety of reactions, some because of the presence of the hydroxide group, others because of the absence of steric hindrance of the methyl group, and still others because the —CH$_2$OH group is bound to the hydrogen atom rather than to another carbon atom. Methanol is, therefore, an important chemical precursor. It is widely used in the manufacture of formaldehyde (20% of total consumption), chloromethanes, acetic acid, methyl acetate and methyl formate. It is also used as an intermediate in the manufacture of acetic anhydride and in the manufacture of dimethyl ether. Methanol also finds increasing use as an octane booster for gasoline by direct blending or as a raw material for methyl tert-butyl ether (MTBE) and for fuel cell applications. Furthermore, there is the exciting discovery that methanol can be converted to high octane gasoline by the Mobil methanol-to-gasoline (MTG) process.

Methanol is currently produced almost solely by reacting synthesis gas ("syngas") comprising hydrogen and carbon monoxide in the presence of a heterogeneous copper catalyst. Methanol was first produced from syngas by Badische Anilin & Soda-Fabrik AG, Germany in 1923, according to the reaction shown in the following equation:

$$2H_2 + CO \rightarrow CH_3OH$$

Zinc/chromium oxide catalyst was used, with a high selectivity for formation of methanol at temperatures between 320° and 380° C., and pressures of 300 to 350 atm. This catalyst along with minor variants was used in the "high pressure" methanol synthesis up to the mid 1960's. The reaction such as described in the above equation, in which methanol is produced from synthesis gas in one step, is often referred to as the "direct synthesis."

In 1966, a new "low pressure" process was developed by The Imperial Chemical Industries ("ICI"). This process uses Cu/ZnO or Cu/ZnO/Al$_2$O$_3$ as a catalyst and operates at 200°–300° C. and 50–110 atm. Today, most methanol is manufactured by this method. The reaction is carried out in the gas phase in a fixed bed reactor. Approximately 6% by volume of $CO_2$ is normally added to the syngas feed. It has been reported that all the MeOH is formed via $CO_2$ rather than CO as discussed by G. C. Chinchen, et al. in *Chemtech*, 692 (November 1990).

The power requirements, good catalyst life, larger capacity single-train convertor designs and improved reliability, of the low pressure technology result in lower energy consumption and economy of scale. However, the low pressure direct process has certain drawbacks. Chief among these drawbacks is the high operating temperature (T=250° C.). Thermodynamic calculations show that, at a temperature of 250° C. and a pressure of 50 atm, 51.9% of the syngas can be converted at equilibrium. These calculations are based upon a stoichiometric H$_2$/CO feed composition of 2 and an assumption of ideal gases. Under present industrial conditions, however, only about 6–12% conversion per pass is typically achieved.

The methanol synthesis reaction is very exothermic. Poor heat transfer in the catalyst bed results in an outlet methanol concentration limited to 5–6 mole %. Either cool unreacted gas injected at stages in the catalyst bed or internal cooling surfaces is generally used to control the bed temperature. To achieve maximum conversion of the carbon oxides, an excess of H$_2$ is used. The excess of H$_2$ requires a high recycle ratio which, in turn, leads to greater expense. Therefore, any modification in the process technology that can enhance heat transfer will result in higher conversions. Furthermore, a decrease in operating temperature could result in lower energy consumption and a higher equilibrium conversion.

To overcome the heat transfer limitation, slurry phase processes are being developed. Processes based on three phase fluidized bed, three phase fixed bed, slurry phase bubble column and mechanically agitated slurry phase reactors are known. These processes take advantage of the outstanding characteristics of a slurry reactor; notably the excellent heat transfer between the catalyst and the liquid, with the liquid serving as a heat sink for the heat of reaction. The use of slurry reactors results in excellent temperature control and higher synthesis gas conversion per pass. These processes, though not yet commercialized, operate at almost the same temperature and pressure as the gas phase process.

A process based on slurry phase technology is the "LaPorte process" being jointly developed by Air Products and Chem Systems. (D. M. Brown and M. I.

Greene, "Catalyst Performance In Liquid Phase Methanol Synthesis", presented at the Summer National Meeting AIChE Meeting, Philadelphia, August 1984). This process has been claimed to be near commercialization. The process development unit incorporates an ebullated slurry bubble column capable of once-through operation on clean coal gasifier effluent gas. The catalyst, which is suspended in the liquid phase, is a Cu/ZnO catalyst. Higher synthesis gas conversions per pass than achieved in gas-phase processes have been reported for the LaPorte process. The use of coal derived synthesis gas which is rich in CO has been reported to yield no substantial difference in the rate of methanol synthesis.

Although the use of slurry reactors provides beneficial results, several problems persist with the current "low pressure" technology. Most importantly, the synthesis temperature is still quite high. Because lower reaction temperatures result in lower free energy change for the reaction, the production of methanol is unfavorable at high temperatures. Temperatures of 240° to 260° C. and high pressures are needed to achieve high reaction rates with the currently used process technology. Therefore, if catalysts with higher activity at lower temperatures could be developed, considerable improvement in the economics of the process would result.

A promising, but little studied, alternate route is a "two-step" synthesis to methanol via methyl formate disclosed in U.S. Pat. No. 1,302,011. The two-step synthesis comprises the carbonylation of a carrier alcohol to the corresponding alcohol formate using alkali alkoxides as homogeneous catalysts. The carbonylation step is followed by hydrogenolysis of the formate on the surface of copper chromite to yield the carrier alcohol and MeOH. The reaction sequence is shown by the following equations: Carbonylation of carrier alcohol,

$$ROH + CO \rightarrow HCOOR$$

Hydrogenolysis of the corresponding formate,

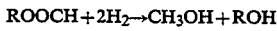

$$ROOCH + 2H_2 \rightarrow CH_3OH + ROH$$

The two individual reactions are well known, the former being the commercial route to methyl formate production. The carbonylation reaction is carried out at temperatures of 80°–100° C. and pressures of 30–50 atm in the presence of a homogeneous catalyst. The carbonylation reaction thus takes place in the liquid phase. The hydrogenolysis of methyl formate can be carried out at temperatures of 100°–160° C. and atmospheric pressure in the presence of a heterogeneous catalyst. Carrying out these two steps in series can result in methanol synthesis at considerably milder conditions. If the carrier alcohol used is MeOH, the reaction yields two moles of MeOH as product. Reaction rates comparable to those obtained commercially and reduced separation costs are obtained by using methanol as the carrier alcohol.

The two-step process has several advantages over the direct methanol synthesis technology, including: lower reaction temperatures; higher synthesis gas conversions per pass (thus decreasing recycle load) and improved heat transfer, because the reaction is carried out in a liquid slurry.

The two-step synthesis process via alkyl formate avoids the thermodynamic limitations of presently practiced methanol synthesis, making the process less energy intensive. The liquid phase acts as a heat sink reducing the heat transfer limitation. When methanol is used as a solvent, mass transfer limitations are reduced. This process thus provides an efficient route to the manufacture of methanol.

A major disadvantage of the two-step process, however, is the need for two reactor systems and two feed preparation systems. A seemingly attractive alternative would be to carry out both reactions concurrently in the same reactor ("concurrent synthesis"). It is not clear, however, that such a combination of reactions would be feasible. Viewed independently, the carbonylation and hydrogenolysis reactions, appear to be incompatible.

Initially, CO, one of the reactants in the carbonylation reaction, inhibits the hydrogenolysis reaction. Furthermore, $CO_2$, which is usually present in syngas, has a strong negative effect on both reactions. The negative effect of $CO_2$ in the carbonylation reaction appears to be irreversible when the $CO_2$ is removed. Finally, selection of an operating temperature must be a compromise between the relatively low temperature required to obtain high conversion in the carbonylation reaction and the higher temperature required to obtain a reasonable rate in the hydrogenolysis reaction.

Experimental evidence showing that the carbonylation and hydrogenolysis reactions can occur at 200° C. and 150–250 atm. in a single reactor containing sodium methoxide (NaOMe) and a copper-chromium-calcium catalyst was provided by Imyanitov, N. B., et al. in *Gidroformilirovanie*, 152 (1972). Evidence showing that the concurrent reaction can occur at 200° C. and 150–250 atm. with sodium carbonate or sodium formate in combination with a copper-chromium-calcium catalyst was also provided.

Aker Engineering, in *Petrole Engineering*, also reported a two-component liquid phase catalytic system to convert syngas to a mixture of methanol and methyl formate in a single reactor. The process was reported to operate typically at 110° C. and 0.5 MPa. Under these conditions the main product would be methyl formate rather than methanol. The report disclosed the use of only alkali and/or alkaline earth alkoxides (alcoholates) as the carbonylation catalyst with copper chromite as the hydrogenolysis catalyst. The report also emphasized, however, the need to eliminate all $CO_2$, $H_2O$ and sulfur compounds from the inlet syngas.

Similarly, U.S. Pat. No. 4,731,386 discloses preparation of methanol from syngas in a liquid reaction mixture in the presence of a catalyst system consisting of an alkali alcoholate and a heterogeneous copper catalyst. It was found that the addition of a non-polar organic solvent having weak cation solvatizing properties in the liquid phase, otherwise consisting of methanol and methylformate, substantially increased the catalytic activity of catalyst systems consisting of an alkali metal alcoholate and a heterogeneous copper catalyst.

Liu, Z., et al., "Methanol Synthesis via Methyl Formate in a Slurry Reactor", 18 *Fuel Processing Technology*, 185 (1988), studied concurrent synthesis in a slurry reaction using $KOCH_3$ and a copper chromite at temperatures of 140°–180° C. and pressures of 3.8–6.2 MPa. Liu, et al. found the results from the concurrent methanol synthesis to be different from those predicted by the individual reactions. Methanol production was found to be higher and the effect of $CO_2$ was lessened and reversible. A "small" amount of water was reported not to be detrimental to catalyst activity. Rates of reaction were found to be comparable to those reported for direct synthesis.

It is thus known that methoxides such as those derived from sodium or potassium or alkaline earth metals such as barium can be used along with a copper chromite catalyst in the concurrent synthesis of methanol. The main drawback of using a catalyst system including methoxides is the high cost required for catalyst manufacture and activity upkeep. Carbonates and formates have similarly been used in the concurrent process, but only at highly elevated temperatures.

The high temperatures currently needed to synthesize methanol via the direct route using copper-zinc catalysts and the high cost of using methoxides as a catalyst make it highly desirable to develop inexpensive alternative catalyst systems which enable methanol synthesis under mild temperatures while achieving high syngas conversion per pass and high methanol selectivity.

SUMMARY OF THE INVENTION

The present invention relates to a novel route for the synthesis of methanol, and more specifically, to the production of methanol by contacting a gaseous mixture of carbon monoxide and hydrogen under relatively mild catalyst comprising reduced copper chromite and a homogeneous catalyst comprising basic compounds of alkali or alkaline earth metals such as the oxide, hydroxide, carbonate, bicarbonate, formate, chromate and the acetate. Homogeneous catalysis concerns reactions carried out in a single phase, while heterogeneous catalytic reactions involve two or more phases. The alkali could be lithium, sodium, potassium, rubidium or cesium. The alkaline earth could be magnesium, calcium or barium. The process produces methanol with up to 90% syngas conversion and up to 95% methanol selectivity. The only major by-products are small amounts of easily separated methyl formate and very small amounts of water, carbon dioxide and dimethyl ether.

DETAILED DESCRIPTION OF THE PREFERRED EMBODIMENT OF THE INVENTION

The present invention relates to a novel route for the synthesis of methanol from syngas using a catalyst combination or system comprising a copper chromite catalyst and basic compounds of alkali metals or alkaline earth metals such as hydroxides, formates, carbonates, oxides, acetates, chromates and bicarbonates.

Suitable basic compounds of alkali metals include the hydroxides, formates, carbonates, bicarbonates, oxides, chromates and acetates of sodium, potassium, rubidium and cesium. Suitable salts of alkaline earth metals include the hydroxides, formates, carbonates, bicarbonates, oxides, chromates, and acetates of magnesium, calcium and barium.

The catalyst system of the present process has the ability to tolerate fluctuations in the $H_2:CO$ ratio without having a major deleterious effect on the reaction rate. Almost no change in the reaction rate is observed in the $H_2:CO$ ratio range of 1.5–2.0:1. The present synthesis route thus enables the use of a wide range of $H_2:CO$ ratios. The $H_2:CO$ ratio can range from 0.5:1 to 3.1. Preferably, the $H_2:CO$ ratio ranges from 1:1 to 3:1. Most preferably, a stoichiometric ratio of 2:1 is used.

Moreover, carbon dioxide in the inlet gas can also be tolerated. Experiments with an inlet gas composition of 0.1–0.3% have been run successfully. However, up to 6% $CO_2$ has been generated during the reaction startup, but the system has the ability to simultaneously tolerate this level of $CO_2$ and self-stabilize itself in terms of the $CO_2$ level. Furthermore, a steady-state outlet concentration of 0.8% is easily tolerated.

Similarly, the presence of water can also be tolerated by the present catalyst system. A steady-state water concentration of 0.2–0.3% in the liquid phase does not seriously effect the reaction rate. This attribute is essential in that water is always present in the liquid phase because of the water-gas shift reaction. The water-gas shift reaction can easily be controlled to keep the water concentration within the acceptable range. However, it is preferable that the reactants be as dry as possible.

The copper content of the copper chromite catalyst is preferably in the range of 30% to 60%. The chromium content of the copper chromite catalyst is preferably in the range of 40% to 60%. The reaction can be carried out in a continuous or semi-continuous manner at temperatures between approximately 100°–160° C., and pressures preferably between approximately 40–65 atm. The feed velocity at which the process is carried out is preferably in the range of 60–140 cc./min. based on a reactor volume of 150 cc., these values being measured at conditions of standard pressure and temperature. The copper-chromite is preferably present in the form of about 1 to 20 wt. % of the slurry. The alkali or alkaline earth compound is preferably present in the form of about 0.1 to 20 wt. %.

Preferably, methanol is used as the carrier alcohol. Although, other alcohols such as ethanol, proponal and higher alcohols can be used as a carrier alcohol, their use may result in undesirable side products and could complicate product recovery.

The methanol produced via this invention may be formed through a methyl formate intermediate or through a surface methoxy group attached to the heterogeneous copper chromite catalyst. Because the alkali and alkaline earth salts enhance the activity of the copper chromite catalyst, the reduced form of this catalyst combination, when reacted with methanol, produces methanol with up to 90% syngas conversion and up to 95% methanol selectivity. Syngas conversions of 95% or more should be easily obtainable when the process is operated in a continuous manner. The high per pass conversion of syngas eliminates or greatly reduces the necessity of recycle. The syngas conversion and methanol selectivity obtained with the present catalyst systems are comparable to those currently achieved by the industrial synthesis of methanol at temperatures of approximately 250° C.

The major by-product of this reaction is a small amount of highly volatile, easily separated, methyl formate. Other by-products include water, $CO_2$ and dimethyl ether, all in considerably smaller quantities. Other oxygenated products or higher alcohols are produced, at most, in trace quantities.

Low deactivation rates for the catalysts were obtained with the present catalyst systems thus ensuring continued catalyst activity. The reduced form of the present catalyst combination, when reacted with methanol, therefore, provides a novel cost efficient route to the synthesis of methanol.

The present process has several advantages over methanol synthesis processes currently in use, including:

1. Methanol can be manufactured by the present process at milder conditions of 100°–160° C. and pressures of 40–65 atmospheres;
2. Up to 95% selectivity to methanol and 90% syngas conversion is obtained, resulting in very low recycle ratios;
3. The only major by-products are small amounts of easily separated methyl formate and very small amounts of water, carbon dioxide and dimethyl ether.
4. Alkali or alkaline earth salts and heterogeneous copper chromite can be used as the catalysts;
5. Methoxides, formates, hydroxides, carbonates, bicarbonates, oxides and acetates of alkali and alkaline earth metals can be used as catalysts;
6. Ethanol is formed at most in trace quantities;
7. High stability and consistent activity are obtained for the catalysts with a low deactivating rate;
8. $CO_2$ is a deactivating agent and should be kept as low as possible. However, peak amounts of up to 6% $CO_2$ may be encountered during process startup. The catalyst is tolerant of these levels. During operation, however, the $CO_2$ level falls sharply to approximately 0.8–1.0%. This level of $CO_2$ is easily tolerated;
9. $H_2O$ is also a deactivating agent and should be kept as low as possible. The level of water during reaction startup is the highest. As the reaction proceeds, however, the level of water drops until a steady state concentration of approximately 0.3–0.5% is reached in the liquid phase. This level is easily tolerated by the catalyst;
10. The catalyst system can tolerate fluctuations in the $H_2:CO$ ratio effectively; and
11. The liquid phase slurry synthesis provides effective temperature control with rates comparable to processes now operated commercially using copper/zinc oxide catalysts.

EXAMPLES

Example 1

In Table 1, the reaction rates obtained using the present process is compared with that obtained with two prior art systems producing methanol via direct synthesis. As seen on Table 1, the present process gives comparable rates at a significantly lower temperature.

TABLE 1

| Reactor type | Temp. (°C.) | Pressure (bar) | Rate of MeOH gmol/h/kg cat | Other conditions |
|---|---|---|---|---|
| Laporte Autoclave, 3 Phase slurry | 250 | 52.12 | 15.2 | CO rich gas 5000 l/h/kgcat S.V. |
| | 250 | 52.12 | 15.8 | Balanced gas 5000 l/h/kgcat S.V. |
| ICI gas phase, Fixed Bed | 225 | 50.0 | 16.7 | Away from equilibrium. |
| Present Synthesis, slurry reactor | 150 | 63.0 | 21.2 | $H_2/CO = 2:1$ 2100 l/h/kgcat S.V. |

The rate presented in Table 1 for the present reaction is for a mixed catalyst comprising 0.5 gms. potassium methoxide and 3 gms. copper chromite in 150 cc. methanol. The per pass conversion for this catalyst combination was 74%.

The advantageous features of the present catalyst systems are further described by the following examples:

Example 2

Synthesis gas having an inlet composition of 66.6% $H_2$, 33.3% CO and 0.1% $CO_2$ was fed to a 300 cc. stainless steel autoclave charged with 3 gms. copper chromite (containing 31.1% copper and 29% chromium), 0.5 gms. potassium methoxide and 150 cc. methanol, reduced in situ using a stream of pure $H_2$ flowing at 25 cc./min. for 16 hours at 170° C. Both catalysts were added separately in the powder form. The reactor was pressurized to 910 psig. and the temperature was adjusted to 150° C., using a temperature controller. Synthesis gas at a flow rate of 105 cc./min. (measured under standard conditions) and a feed $H_2/CO$ ratio of 2, was made to react under isothermal conditions. After an initial transient period, the process reached a steady state with respect to the amount of synthesis gas converted. A methanol production rate based on $H_2$ consumption of 21.2 gmoles/h/kg. cat was obtained with 74% syngas conversion and 95% selectivity towards methanol. An exit gas composition of 66% $H_2$, 32% CO, 0.8% $CO_2$, 0.7% methanol, 0.4% methyl formate, 0.2% $H_2O$ and 0.07% dimethyl ether was obtained. A liquid composition of 95.6% methanol, 4% methyl formate, 0.3% water and traces of dimethyl ether and dissolved gases was obtained.

Example 3

Different catalysts comprising methoxides, hydroxides, formates, carbonates and bicarbonates of sodium, potassium, rubidium and cesium were individually added to the reactor in equimolar quantities along with copper chromite and methanol. The catalysts were identically reduced in a stream of $H_2$ for 16 hours at 170° C. Synthesis gas, as described in Example 1, was bubbled through the reactor. All the individual catalysts added were active at 150° C. and 910 psig. No higher alcohols were obtained in any of the runs. Almost identical liquid composition as recorded in Example 2 was obtained. The alkali promotes the methanol synthesis reaction by enhancing the activity of the copper chromite catalysts.

Example 4

The effects of $CO_2$ during the initial transient period were studied in experiments in which synthesis gas was introduced into the reactor charged with 17.75 gms. copper chromite (containing 31.1% copper and 29% chromium), 2.958 gms. potassium methoxide and 150 cc. methanol followed by a procedure as described in Example 2. The $CO_2$ content of the feed gas was 0.1%. As the reaction progressed, the $CO_2$ content of the exit gas climbed steadily to a maximum concentration of approximately 6% after 4 hours. The rate of reaction was a minimum at this maximum $CO_2$ concentration. Subsequently, the $CO_2$ content slowly stabilized itself to reach a steady-state composition of 0.8% in the exit gas. As the $CO_2$ concentration decreased, the rate of reaction increased, climbing to a maximum of 2.6 gmoles/h/kg. cat after approximately 35 hours of operation. The catalyst system is thus tolerant to fluctuations in the $CO_2$ level and the poisoning effect of $CO_2$ upon the catalyst is reversible. Furthermore, the process has the ability to stabilize the level of $CO_2$ in the reaction mixture.

Example 5

Stabilization of $CO_2$ concentration as observed in Example 4 was also noted for experiments with catalysts described in Example 2. Using a mixed catalyst comprised of potassium hydroxide and copper chromite, peak amounts of up to 4.2% $CO_2$ were observed in the gas during startup. This level self-stabilized to about 0.8% as the reaction progressed. The catalyst had the ability to tolerate this amount of $CO_2$ during startup. Similarly peak amounts of up to 4.1% were observed using a mixed catalyst comprised of potassium formate and copper chromite during startup, the $CO_2$ stabilizing itself at around 0.7% as the reaction progressed. Peak amounts of up to 4.17% $CO_2$ were also observed in the case of a mixed catalyst comprised of cesium chromate and copper chromite, the $CO_2$ stabilizing to 0.6% as the reaction progressed. The catalyst system is thus tolerant of fluctuations in the $CO_2$ level in the gas.

Example 6

The rate of deactivation of the present methanol synthesis catalyst was studied in reactions involving all of the catalyst combinations described in Example 2. Each combination displayed low deactivation rates even in the presence of $CO_2$ and $H_2O$. The longest experimental run was performed for a period of 120 hours. In general, the rate of deactivation decreased in the order of $Cs>Rb>K>Na$.

Example 7

Synthesis gas having an inlet composition of 6.6% $H_2$, 33.3% CO and 0.1% $CO_2$ was fed to a 300 cc. stainless steel autoclave charged with 3 gms. copper-chromite (containing 31.1% copper and 29% chromium), 2.185 gms. barium oxide and 150 cc. methanol, reduced in situ using a stream of pure $H_2$ flowing at 25 cc/min. for 16 hrs. at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 2.3 gmoles/h/kg catalyst was obtained with 9% synthesis gas conversion and 95% selectivity towards methanol. An exit gas composition of 65.7% $H_2$, 32% CO, 0.8% $CO_2$, 1.0% methanol, 0.3% methyl formate, 0.1% $H_2O$ and 0.02% dimethyl ether was obtained. A liquid composition of 95.6% methanol, 4.0% methyl formate, 0.3% water and traces of dimethyl ether and dissolved gases was obtained at the end of the run.

Example 8

Synthesis gas having an inlet composition of 66.6% $H_2$, 33.3% CO and 0.1% $CO_2$ was fed to a 300 cc. stainless steel autoclave charged with 3 gms. copper-chromite (containing 31.1% copper and 29% chromium), 0.48 gm. potassium hydroxide and 150 cc. methanol, reduced in situ using a stream of pure $H_2$ flowing at 25 cc/min. for 16 hrs. at 170° C. Both catalysts were added separately in the powder form. The reactor was pressurized to 910 psig. and the temperature was adjusted to 150° C. Synthesis gas at a flow rate of 87 cc/min. (measured under standard conditions) was made to react under isothermal conditions. After an initial transient period, the process reached a steady state with respect to the amount of synthesis gas converted. A methanol production rate based on $H_2$ consumption of 21.2 gmoles/h/kg. cat. was obtained with 89.5% synthesis gas conversion and 95% selectivity towards methanol. An exit gas composition of 62% $H_2$, 34.8% CO, 0.46% $CO_2$, 1.5% methanol, 1.0% methyl formate, 0.2% $H_2O$ and 0.07% dimethyl ether was obtained. A liquid composition of 95.6% methanol, 4% methyl formate, 0.3% water and traces of dimethyl ether and dissolved gases was obtained.

Example 9

Synthesis gas having an inlet composition of 66.6% $H_2$, 33.3% CO and 0.1% $CO_2$ was fed to a 300 cc. stainless steel autoclave cahrged with 3 gms. copper-chromite (containing 31.1% copper and 29% chromium), 0.8 gm. potassium hydroxide and 150 cc. methanol, reduced in situ using a stream of pure $H_2$ flowing at 25 cc/min. for 16 hours at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 17.83 gmoles/h/kg catalyst was obtained with 61% synthesis gas conversion and 95% selectivity towards methanol. An exit gas composition of 64% $H_2$, 34% CO, 0.8% $CO_2$, 0.7% methanol, 0.4% methyl formate, 0.2% $H_2O$ and 0.07% dimethyl ether was obtained. A liquid composition of 95.6% methanol, 4% methyl formate, 0.3% water and traces of dimethyl ether and dissolved gases was obtained.

Example 10

Synthesis gas having an inlet composition of 66.6% $H_2$, 33.3% CO and 0.1% $CO_2$ was fed to a 300 cc. stainless steel autoclave charged with 3 gms. copper-chromite (containing 31.1% copper and 29% chromium), 1.67 gms. cesium bicarbonate and 150 cc. methanol, reduced in situ using a stream of pure $H_2$ flowing at 25 cc/min. for 16 hours at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 15.66 gmoles/h/kg catalyst was obtained with 54% synthesis gas conversion and 95% selectivity towards methanol. An exit gas composition of 63% $H_2$, 35% CO, 0.8% $CO_2$, 0.7% methanol, 0.4% methyl formate, 0.2% $H_2O$ and 0.07% dimethyl ether was obtained. A liquid composition of 95.6% methanol, 4% methyl formate, 0.3% water and traces of dimethyl ether and dissolved gases was obtained.

Example 11

Synthesis gas having an inlet composition of 66.6% $H_2$, 33.3% CO and 0.1% $CO_2$ was fed to a 300 cc. stainless steel autoclave charged with 3 gms. copper-chromite (containing 31.1% copper and 29% chromium), 2.185 gms. barium oxide and 150 cc. methanol, reduced in situ using a stream of pure $H_2$ flowing at 25 cc/min. for 16 hours at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 2.3 gmoles/h/kg catalyst was obtained with 9% synthesis gase conversion and 95% selectivity towards methanol. An exit gas composition of 65.7% $H_2$, 32% CO, 0.8% $CO_2$, 1.0% methanol, 0.3% methyl formate, 0.1% $H_2O$ and 0.02% dimethyl ether was obtained. A liquid composition of 95.6% methanol, 4.0% methyl formate, 0.3% water and traces of dimethyl ether and dissolved gases was obtained at the end of the run.

Example 12

Synthesis gas having an inlet composition of 66.6% $H_2$, 33.3% CO and 0.1% $CO_2$ was fed to a 300 cc. stainless steel autoclave charged with 3 gms. copper-chromite (containing 31.1% copper and 29% chromium), 1.2 gm. potassium formate and 150 cc. methanol, reduced in situ using a stream of pure $H_2$ flowing at 25 cc/min. for 16 hours at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 17.16 gmoles/h/kg catalyst was obtained with 60% synthesis gas conversion and 95% selectivity towards methanol. An exit gas composition of 62% $H_2$, 36% CO, 0.7% $CO_2$, 0.6% methanol, 0.4% methyl formate, 0.1% $H_2O$ and 0.07% dimethyl ether was obtained. A liquid composition of 95.4% methanol, 4% methyl formate, 0.3% water and traces of dimethyl ether and dissolved gases was obtained.

Example 13

Synthesis gas having an inlet composition of 66.6% $H_2$, 33.3% CO and 0.1% $CO_2$ was fed to a 300 cc. stainless steel autoclave charged with 3 gms. copper-chromite (containing 31.1% copper and 29% chromium), 1.36 gms. of cesium chromate and 150 cc. methanol, reduced in situ using a stream of pure $H_2$ flowing at 25 cc/min. for 16 hours at 170° C. Both catalysts were added separately in the powder form. The reactor was pressurized to 910 psig. and the temperature was adjusted to 150° C. Synthesis gas at a flow rate of 105 cc/min. (measured under standard conditions) was made to react under isothermal conditions. After an initial transient period, the process reached a steady state with respect to the amount of synthesis gas converted. A methanol production rate based on $H_2$ consumption of 11.44 gmoles/h/kg catalyst was obtained with 50% synthesis gas conversion and 95% selectivity towards methanol. An exit gas composition of 63.55% $H_2$, 33.75% CO, 0.45% $CO_2$, 1.1% methanol, 1.0% methyl formate, 0.125% $H_2O$ and 0.004% dimethyl ether was obtained. A liquid composition of 95.6% methanol, 4% methyl formate, 0.3% water and traces of dimethyl ether and dissolved gases was obtained.

Although the invention has been described in detail for purposes of illustration, it is to be understood that such detail is solely for that purpose and that variations can be made therein by those skilled in the art without departing from the spirit and scope of the invention except as it may be limited by the claims.

What is claimed is:

1. A process for the slurry synthesis of methanol from a gaseous mixture comprising carbon monoxide and hydrogen, the process comprising the step of adding to a carrier alcohol a catalyst combination comprising copper chromite and a basic alkali metal compound selected from the group consisting of oxides, hydroxides, formates, carbonates, bicarbonates, chromates and acetates, in an amount effective to catalyze the synthesis of methanol via a carbonylation/hydrogenolysis concurrent synthesis, in which the carrier alcohol undergoes carbonylation to yield in corresponding alkyl formate and the alkyl formate undergoes hydrogenolysis to yield methanol and the carrier alcohol, said basic alkali metal compound being solubilized in said carrier alcohol during methanol synthesis.

2. The process of claim 1 wherein the alkali metal present in the alkali metal compound is selected from the group consisting of sodium, potassium, rubidium and cesium.

3. The process of claim 1 wherein the copper chromite is present in from about 1 to 20 wt. %.

4. The process of claim 3 wherein the alkali metal compound is present in from about 0.1 to 20 wt. %.

5. The process of claim 1 wherein the copper content of copper chromite is present in the range of 30 to 60 wt. %, weight of copper chromite.

6. The process of claim 1 wherein the chromium content of copper chromite is present in the range of 40 to 60 wt. %, based on the weight of copper chromite.

7. The process of claim 1 wherein synthesis temperature is between about 100° and 160° C.

8. The process of claim 1 wherein synthesis pressure is between about 40 and 65 atmospheres.

9. The process of claim 1 wherein the carrier alcohol is methanol.

10. The process of claim 1 wherein a per pass conversion of at least 90% is achieved.

11. A process for the slurry synthesis of methanol from a gaseous mixture comprising carbon monoxide and hydrogen, the process comprising the step of adding to a carrier alcohol a catalyst combination comprising copper chromite and a basic alkaline earth metal compound selected from the group consisting of oxides, hydroxides, formates, carbonates, bicarbonates, chromates and acetates, in an amount effective to catalyze the synthesis of methanol via a carbonylation/hydrogenolysis concurrent synthesis, in which the carrier alcohol undergoes carbonylation to yield in corresponding alkyl formate and the alkyl formate undergoes hydrogenolysis to yield methanol and the carrier alcohol, said basic alkaline earth metal compound being solubilized in said carrier alcohol during methanol synthesis.

12. The process of claim 11 wherein the alkaline earth metal present within the alkaline earth compound is selected from the group consisting of calcium, magnesium or barium.

13. The process of claim 11 wherein the copper chromite is present in from about 1 to 20 wt. %.

14. The process of claim 13 wherein the alkali metal compound is present in from about 0.1 to 20 wt. %.

15. The process of claim 11 wherein the copper content of copper chromite is present in the range of 30 to 60 wt. %, weight of copper chromite.

16. The process of claim 11 wherein the chromium content of copper chromite is present in the range of 40 to 60 wt. %, based on the weight of copper chromite.

17. The process of claim 11 wherein synthesis temperature is between about 100° and 160° C.

18. The process of claim 11 wherein synthesis pressure is between about 40 and 65 atmospheres.

19. The process of claim 11 wherein the carrier alcohol is methanol.

20. The process of claim 11 wherein a per pass conversion of at least 90% is achieved.

* * * * *